(12) United States Patent
Hallbäck

(10) Patent No.: US 12,370,334 B2
(45) Date of Patent: Jul. 29, 2025

(54) VENTILATOR ARRANGEMENT AND METHOD FOR CONTROLLING A VENTILATOR ARRANGEMENT

(71) Applicant: MAQUET CRITICAL CARE AB, Solna (SE)

(72) Inventor: Magnus Hallbäck, Danderyd (SE)

(73) Assignee: MAQUET CRITICAL CARE AB, Solna (SE)

(*) Notice: Subject to any disclaimer, the term of this patent is extended or adjusted under 35 U.S.C. 154(b) by 0 days.

(21) Appl. No.: 18/649,257

(22) Filed: Apr. 29, 2024

(65) Prior Publication Data
US 2024/0285888 A1    Aug. 29, 2024

Related U.S. Application Data

(63) Continuation of application No. 15/733,475, filed as application No. PCT/SE2019/050098 on Feb. 6, 2019, now Pat. No. 11,998,691.

(30) Foreign Application Priority Data

Feb. 6, 2018 (SE) .................... 1850135-3

(51) Int. Cl.
*A61M 16/00* (2006.01)
*A61B 5/091* (2006.01)
*A61M 16/20* (2006.01)

(52) U.S. Cl.
CPC .......... *A61M 16/024* (2017.08); *A61B 5/091* (2013.01); *A61M 2016/0027* (2013.01); *A61M 2016/0036* (2013.01); *A61M 16/205* (2014.02); *A61M 2205/15* (2013.01); *A61M 2205/52* (2013.01); *A61M 2205/581* (2013.01); *A61M 2205/582* (2013.01); *A61M 2205/583* (2013.01); *A61M 2230/40* (2013.01)

(58) Field of Classification Search
CPC .............. A61M 16/024; A61M 16/205; A61M 2016/0027; A61M 2016/0036; A61M 2205/15; A61M 2205/52; A61M 2205/581; A61M 2205/582; A61M 2205/583; A61M 2230/40; A61M 16/12; A61M 16/204; A61M 2016/0039; A61M 2016/0042; A61M 2205/50; A61M 2205/502; A61M 2205/505; A61M 2230/432; A61B 5/091
USPC ............ 128/204.23, 204.21, 204.18, 200.24, 128/203.14, 204.22, 205.19
See application file for complete search history.

(56) References Cited

U.S. PATENT DOCUMENTS

| | | | |
|---|---|---|---|
| 2005/0004512 A1* | 1/2005 | Campbell | A61B 17/3421 606/167 |
| 2012/0330199 A1* | 12/2012 | Lurie | A61H 9/0078 601/41 |
| 2013/0174846 A1* | 7/2013 | Stenqvist | A61B 5/085 128/204.23 |

(Continued)

*Primary Examiner* — Victoria Murphy
*Assistant Examiner* — Tina Zhang
(74) *Attorney, Agent, or Firm* — Fay Kaplun & Marcin, LLP

(57) ABSTRACT

A method for controlling a ventilator arrangement might be suitable for maintaining or achieving a desired end expiratory lung volume, EELV, of a subject when an external manoeuvre is performed on the subject ventilated by the ventilator arrangement. The ventilator arrangement applies a set positive end-expiratory pressure, PEEP, level for performing the ventilation.

14 Claims, 5 Drawing Sheets

(56) References Cited

U.S. PATENT DOCUMENTS

| | | | |
|---|---|---|---|
| 2015/0265833 A1* | 9/2015 | Meyyappan | H03M 9/00 |
| 2017/0028145 A1* | 2/2017 | Kuzelka | A61M 16/0051 |
| 2019/0015614 A1* | 1/2019 | Alahmadi | A61B 5/082 |

* cited by examiner

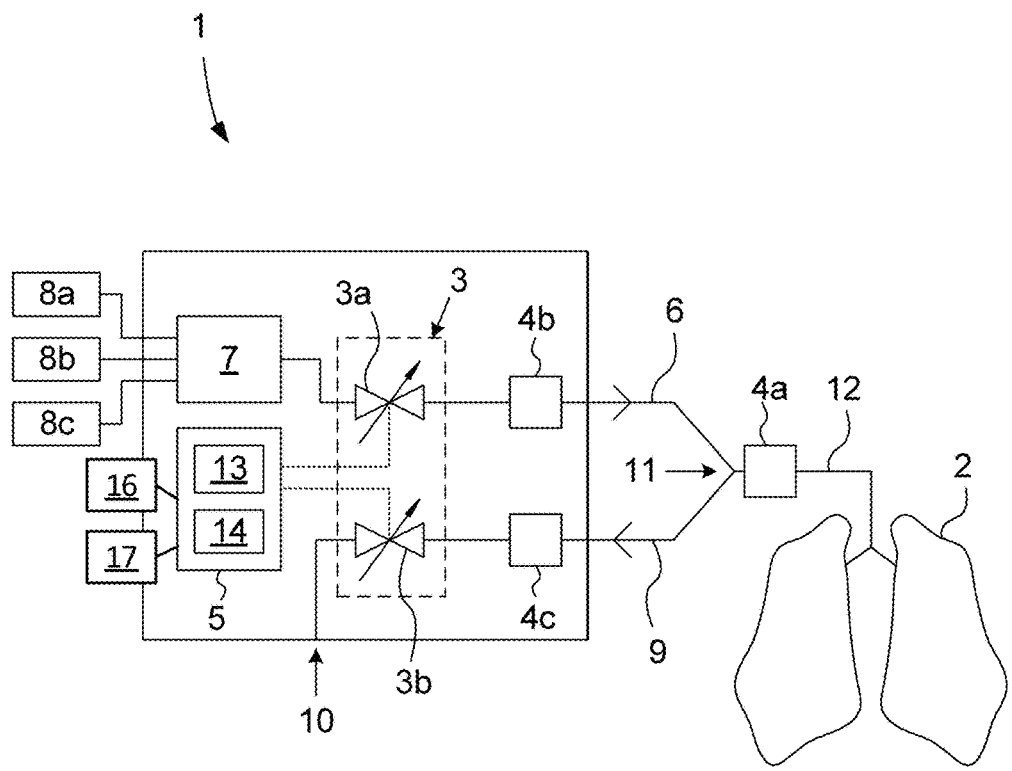
Fig. 1
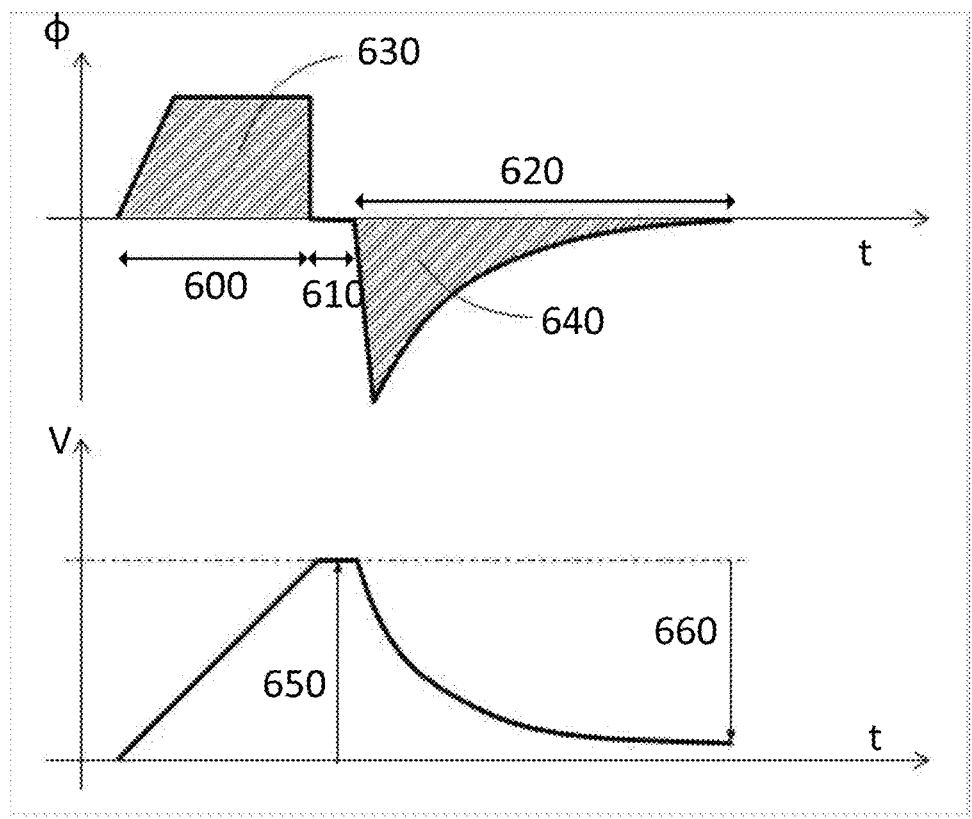
Fig. 6A
Fig. 6B

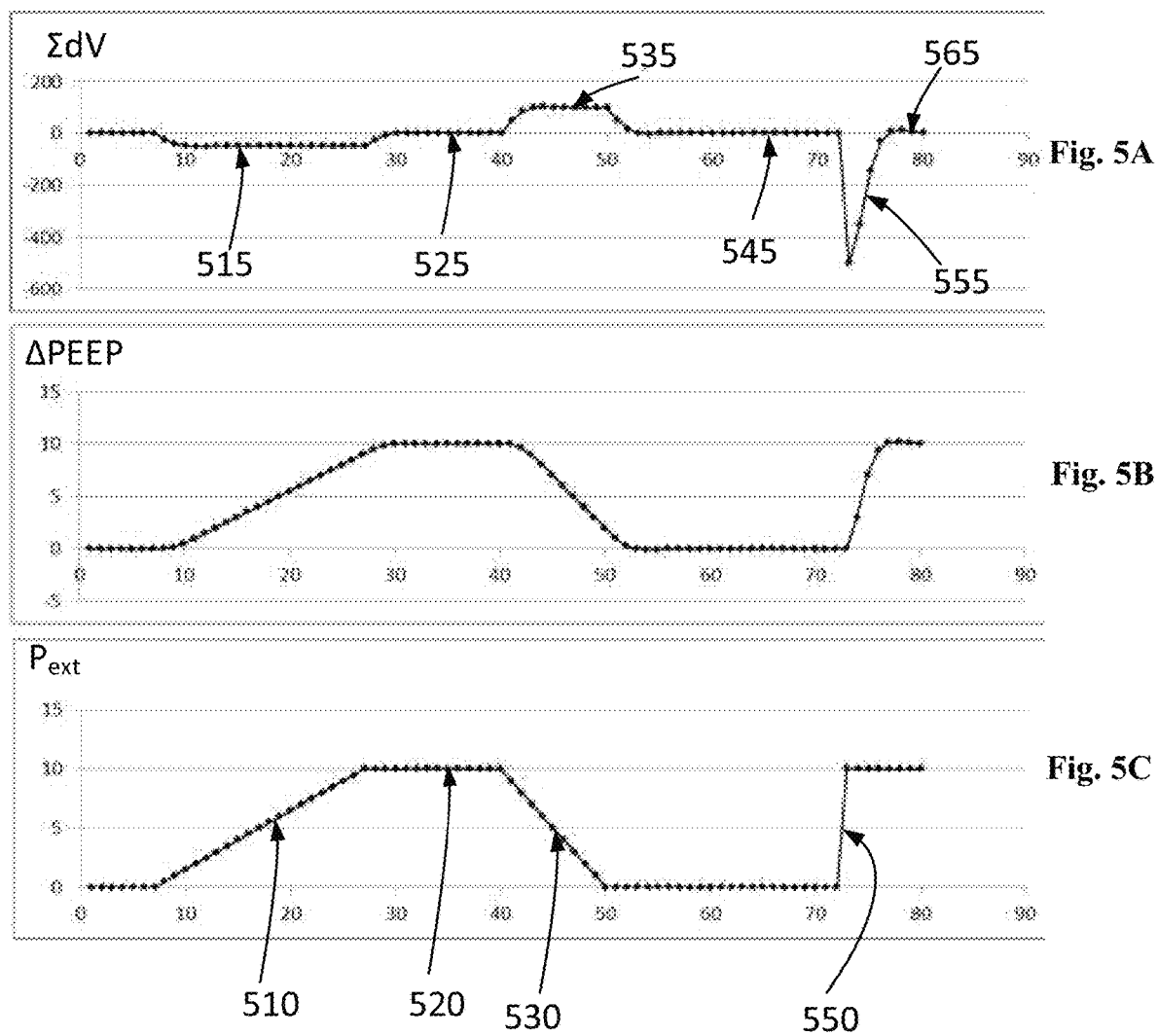

VENTILATOR ARRANGEMENT AND METHOD FOR CONTROLLING A VENTILATOR ARRANGEMENT

TECHNICAL FIELD

The present disclosure relates to a ventilator arrangement and method for controlling a ventilator arrangement. The present disclosure further relates to a computer-readable medium and to a computer program product.

BACKGROUND ART

When using extrathoracic forces or any other external manoeuvre affecting the abdomen it is important to maintain the end expiratory lung volume of a subject. An example might be the changing of position of a subject from horizontal position to the so-called Trendelenburg position. In this case, the weight of the abdomen will expose extra pressure to the diaphragm and thus the lungs, so that the lung volume might get affected. Another example might be pressurising the abdomen with $CO_2$ during laparoscopic surgery which might affect the lung volume due to the extra pressure from the abdomen which exposes the lungs. During an external manoeuvre, such as those described above, the subject might be connected to a ventilator arrangement, for example in preparation for surgery.

In case the lung volume is not maintained during external manoeuvres, regions of the lung might collapse which in its turn requires extra resources for recovering the lung. Further, a lung collapse might require a lung recruitment manoeuvre adding unnecessary stress on the lung tissue, and should thus be avoided. There is thus a need to operate a ventilator arrangement in such a way as to assure that the end expiratory lung volume, EELV, of a subject is maintained when an external manoeuvre is performed on the subject, or, in general, that a desired EELV is achieved in this case.

The ventilator arrangement might provide functionality to apply a set level for positive end-expiratory pressure, PEEP. When using such a ventilator arrangement, it is desirable that the ventilator arrangement is controlled in such a way that the end expiratory lung volume and/or the lung compliance achieved by the PEEP-setting is/are maintained even during and after the external manoeuvre.

SUMMARY OF THE INVENTION

The present invention relates to a ventilator arrangement, a method for controlling a ventilator arrangement, a computer program product, and a computer-readable medium which maintain the end expiratory lung volume, EELV, of a subject when an external manoeuvre is performed on the subject ventilated by the ventilator arrangement.

The present invention relates to a ventilator arrangement, a method for controlling a ventilator arrangement, a computer program product, and a computer-readable medium which achieve a desired end expiratory lung volume, EELV, when an external manoeuvre is performed on a subject ventilated by the ventilator arrangement.

The present invention relates to an alternative ventilator arrangement, an alternative method for controlling a ventilator arrangement, an alternative computer program product, and an alternative computer-readable medium.

The present invention relates to a ventilator arrangement, a method for controlling a ventilator arrangement, a computer program product, and a computer-readable medium which reduces needs and/or time for personal to adjust settings of a ventilator arrangement in connection to performing an external manoeuvre at the subject.

The present invention relates to a ventilator arrangement, a method for controlling a ventilator arrangement, a computer program product, and a computer-readable medium which reduces potential needs for any recovery measures at the subject when or after performing an external manoeuvre at the subject.

The present invention relates to a method for controlling a ventilator arrangement for maintaining the end expiratory lung volume, EELV, of a subject when an external manoeuvre is performed on the subject ventilated by the ventilator arrangement. The ventilator arrangement applies a set positive end-expiratory pressure, PEEP, level for performing the ventilation. The method comprises the step of performing a ventilation pause in the ongoing ventilation of the subject prior to the external manoeuvre. The method further comprises the step of determining a possible change in airway pressure ($\Delta Paw$) of the subject during pausing of the ventilation. The method even further comprises the step of resuming the ventilation of the subject after at least parts of the external manoeuvre. Therein an updated set level for the PEEP is applied. The updated set level basically corresponds to the sum of the set PEEP level prior to pausing the ventilation and the determined possible change in airway pressure ($\Delta Paw$) of the subject.

In this way the method takes care of potential changes in the pressure to which the lungs are exposed to. The EELV is thus maintained. Thus, the risk of lung collapses and the need for lung recovery is reduced. Further, the ventilator arrangement can take care of the adaption itself without the need from the personal to change set-values of the ventilator arrangement. Even further, an adaption of the PEEP-level can be provided without any delay. Thus complexity is reduced. Further, a situation is created which allows performing an external manoeuvre at the subject in a safer way.

In one example, the pausing of the ventilation is initiated by a manual action on an input means of the ventilator arrangement. This allows the personal to reduce the amount of time for which the ventilation is paused, for example by initiation that part of the method only when the subject is ready for the external manoeuvre.

In one example, the resumption of the ventilation starts at a first pre-determined time period after pausing the ventilation. This assures that the ventilation is not paused too long. This helps reducing or avoiding risks to the subject by pausing of the ventilation.

In one example, the method further comprises the step of indicating the resumption of the ventilation a second predetermined time period prior to resuming the ventilation. This can warn the personal that the external manoeuvre has to come to an end, or at least to a pause. This avoids or reduces the risks to the subject which might be caused by a pause in ventilation and/or the external manoeuvre itself.

In one example, the resumption of the ventilation is initiated by a manual action on an input means of the ventilator arrangement. This allows giving the personal full control of the time when the ventilator arrangement resumes ventilation. Thus a high flexibility is achieved. Further, in case the external manoeuvre is performed faster than expected, the ventilation might be resumed earlier. Thus the pause in ventilation can be reduced to a minimum.

In one example, the ventilation of the subject is paused during an expiration phase. This usually implies that the thoracic pressure is comparably smaller, which can give advantages from a haemodynamic point of view. The ventilation can be paused at the end of the expiration phase or at any other time during the expiration phase.

In one example, the ventilation of the subject is paused during an inspiration phase. Since there is usually more air in the lungs during inspiration, especially at the end of an inspiration phase, the subject might tolerate a larger ventilation pause in a safer way. The ventilation can be paused at the end of the inspiration phase or at any other time during the inspiration phase.

In one example, the external manoeuvre is divided in several sub-steps with pauses in between the sub-steps. The method is repeated for each sub-step of the external manoeuvre. This allows using the method even for external manoeuvres requiring a longer time period. As an example, in case the time period of the external manoeuvre might exceed the time period for which the ventilation of the subject safely can be paused, the division into sub-steps, where each subject has a suitable time length, such as a time length not exceeding the time length for which the ventilation of the subject can be safely paused, might allow still using the method although the comparably long manoeuvre.

In one example, the method comprises the step of determining start conditions including at least breathing circuit leakage. This can provide a more accurate method.

In one example, the start conditions also include determining a tidal volume, TV, of the subject. This might be a useful quantity for improving accuracy of the method.

The present invention relates to a ventilator arrangement for maintaining the end expiratory lung volume, EELV, of a subject when an external manoeuvre is performed on the subject ventilated by the ventilator arrangement. The ventilator arrangement is arranged to apply a set positive end-expiratory pressure, PEEP, level for performing the ventilation. The ventilator arrangement is further arranged to performing a ventilation pause in the ventilation of the subject prior to the external manoeuvre. The ventilator arrangement is even further arranged to determining a possible change in airway pressure (ΔPaw) of the subject during pausing of the ventilation. The ventilator arrangement is yet even further arranged to resuming the ventilation of the subject after at least parts of the external manoeuvre. Thereby an updated set level for the PEEP is applied. The updated set level basically corresponds to the sum of the set PEEP level prior to pausing the ventilation and the determined possible change in airway pressure (ΔPaw) of the subject.

In one embodiment, the ventilator arrangement is arranged to initiate the pause of the ventilation based on a manual action on an input means of the ventilator arrangement.

In one embodiment, the ventilator arrangement is arranged to resume the ventilation at a first pre-determined time period after pausing the ventilation.

In one embodiment, the ventilator arrangement is arranged to indicate the resumption of the ventilation a second pre-determined time period prior to resuming the ventilation.

In one embodiment, the ventilator arrangement is arranged to initiate the resumption of the ventilation based on a manual action on an input means of the ventilator arrangement.

In one embodiment, the ventilator arrangement is arranged to pause the ventilation of the subject during an expiration phase. In one embodiment, the ventilator arrangement is arranged to pause the ventilation of the subject at the end of an expiration phase.

In one embodiment, the ventilator arrangement is arranged to pause the ventilation of the subject during an inspiration phase. In one embodiment, the ventilator arrangement is arranged to pause the ventilation of the subject at the end of an inspiration phase.

In one embodiment, the ventilator arrangement is arranged to determine start conditions including at least breathing circuit leakage.

In one embodiment, the start conditions also include determining a tidal volume, TV, of the subject.

The present invention relates to a computer program product, comprising instructions which, when the program is executed by a computer, cause the computer to carry out the method for controlling a ventilator arrangement for maintaining the end expiratory lung volume, EELV, of a subject according to the present disclosure.

The present invention relates to a computer-readable medium comprising instructions which, when executed by a computer, cause the computer to carry out the method for controlling a ventilator arrangement for maintaining the end expiratory lung volume, EELV, of a subject according to the present disclosure.

The present invention relates to a method for controlling a ventilator arrangement for achieving a desired end expiratory lung volume, EELV, when an external manoeuvre is performed on a subject ventilated by the ventilator arrangement. The ventilator arrangement applies a set positive end-expiratory pressure, PEEP, level for performing the ventilation. The method comprises the step of determining a difference between inspired and expired tidal lung volume of a breathing cycle of the subject. The method further comprises the step of adjusting the PEEP level after the breathing cycle of the subject based on the determined difference so that the desired EELV of the subject is achieved. The steps are repeated for several breathing cycles during and/or after the external manoeuvre. Preferably, the steps are repeated for several breathing cycles during the external manoeuvre, and most preferably for basically each breathing cycle during the external manoeuvre.

This allows achieving a desired EELV without the need to pause the ventilation. Thus, the method can be applied even when the ventilator arrangement is used for subjects who cannot safely bear a pausing in the ventilation. The desired EELV might be to keep the EELV constant. The risk of lung collapses and the need for lung recovery is reduced. Further, the ventilator arrangement can take care of the adaption itself without the need from the personnel to find out suitable set-values for the ventilator arrangement. Thus complexity is reduced. Further, a situation is created which allows performing an external manoeuvre at the subject in a safer way.

In one example, the desired EELV is that the EELV is kept basically constant.

In one example, the desired EELV is that the EELV is increased or decreased with a pre-determined amount. This is especially useful in case it is determined that external manoeuvre will require or at least recommend a higher or lower EELV after the performance of the manoeuvre.

In one example, the method further comprises the steps of determining a change in end expiratory lung volume of the subject based on the determined difference between inspired and expired tidal lung volume, and adjusting the PEEP level after the breathing cycle of the subject based on the determined change in end expiratory lung volume.

The change in end expiratory lung volume may be determined based on the determined difference between inspired and expired tidal lung volume and a determined or assumed offset between inspired and expired lung volume of the subject prior to the external manoeuvre. The offset may be assumed to be zero, in which case the change in end expiratory lung volume may be assumed to correspond to the determined difference between inspired and expired tidal lung volume. In other situations, the offset between inspired and expired tidal lung volume may be determined prior to the external manoeuvre. By determining the offset prior to the external manoeuvre and adjusting the PEEP level also based on the determined offset, potential leakage in the ventilator arrangement can be compensated for in a relatively easy manner.

In one example, the method further comprises the step of determining whether a leakage is present in the breathing circuit prior performing the external manoeuvre and outputting a warning in case the presence of a leakage has been determined. This allows for the personal to be extra careful during the external manoeuvre, to not perform the external manoeuvre, or to first trying decreasing the leakage prior performing the manoeuvre.

In one example, the method further comprises the step of determining a flow of breathing gas to and/or from the subject. The inspired and/or expired lung volume is determined based on the determined flow of breathing gas. This provides a practical way for determining the inspired and/or expired breathing gas.

In one example, the repeated steps are repeated for less than about 50 or for less than about 100 breathing cycles. This reduces the risks of potential measurement errors, such as systematic measurement errors. Especially potential measurement errors in determining the difference between inspired and expired tidal lung volume of a breathing cycle of the subject might add up over several breathing cycles. Thus, repeating the method for not too many iterations might increase the safety for the subject.

The present invention relates to a ventilator arrangement. The ventilator arrangement is arranged to apply a set positive end-expiratory pressure, PEEP, level for performing a ventilation of a subject. The ventilator arrangement is further arranged to determine a difference between inspired and expired tidal lung volume of a breathing cycle of the subject.

The ventilator arrangement is even further arranged to adjust the PEEP level after the breathing cycle of the subject based on the determined difference so that a desired end expiratory lung volume, EELV, of the patient is achieved. The ventilator arrangement is arranged to perform the determining and the adjusting repeatedly for several breathing cycles during and/or after the external manoeuvre. Preferably, the steps are repeated for several breathing cycles during the external manoeuvre, and most preferably for basically each breathing cycle during the external manoeuvre.

The ventilator arrangement may be arranged to determine a change in end expiratory lung volume of the subject based on the determined difference between inspired and expired tidal lung volume and to adjust the PEEP level after the breathing cycle of the subject based on the determined change in end expiratory lung volume, in accordance with the above described principles.

In one embodiment, the desired EELV is that the lung volume is kept basically constant.

In one embodiment, the desired EELV is that the lung volume is increased or decreased with a pre-determined amount.

In one embodiment, the ventilator arrangement is further arranged to determine an offset between inspired and expired lung volume (VTi-VTE) prior the external manoeuvre. The adjusting of the PEEP level is also based on the determined offset.

In one embodiment, the ventilator arrangement is arranged to determine whether a leakage is present in the breathing circuit prior performing the external manoeuvre and to output a warning in case the presence of a leakage has been determined.

In one embodiment, the ventilator arrangement is arranged to determine a flow of breathing gas to and/or from the subject. The ventilator arrangement is further arranged to determine the inspired and/or expired lung volume based on the determined flow of breathing gas.

In one embodiment, the ventilator arrangement is arranged to repeat the repeatedly performed steps for less than about 50 or for less than about 100 breathing cycles.

The present invention relates to a computer program product, comprising instructions which, when the program is executed by a computer, cause the computer to carry out the method for controlling a ventilator arrangement for achieving a desired end expiratory lung volume, EELV, when an external manoeuvre is performed on a subject ventilated by the ventilator arrangement according to the present disclosure.

The present invention relates to a computer-readable medium comprising instructions which, when executed by a computer, cause the computer to carry out the method for controlling a ventilator arrangement for achieving a desired end expiratory lung volume, EELV, when an external manoeuvre is performed on a subject ventilated by the ventilator arrangement according to the present disclosure.

The ventilator arrangement, the computer program product and the computer-readable storage medium have corresponding advantages as have been described in connection with the corresponding examples of the corresponding method according to this disclosure.

Further advantages of the present invention are described in the following detailed description and/or will arise to a person skilled in the art when performing the invention.

BRIEF DESCRIPTION OF THE DRAWINGS

For a more detailed understanding of the present invention and its objects and advantages, reference is made to the following detailed description which should be read together with the accompanying drawings. Same reference numbers refer to same components in the different figures. In the following, FIG. 1 shows, in a schematic way, an example of a ventilator arrangement;

FIG. 5a-c show, in a schematic way, an example of a fourth situation in which a method according to the second example of the present disclosure can be used; and FIG. 6a-b show, in a schematic way, an example of a how physical quantities can evolve when using a method according to the second example of the present disclosure.

DETAILED DESCRIPTION

Figure 2A:
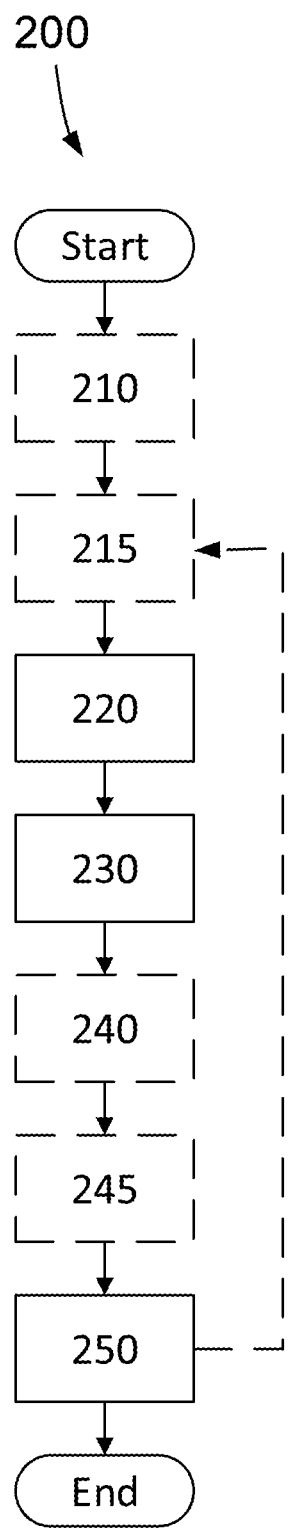
FIG. 2a shows, in a schematic way, a method according to a first example of the present invention.

FIG. 1 shows, in a schematic way, an example of a ventilator arrangement 1 according to the present disclosure. FIG. 1 has been chosen to illustrate the principle of the present disclosure. It should be emphasised that FIG. 1 is only one example and that ventilator arrangements can differ greatly. Thus, even ventilator arrangements looking schematically completely different will be within the scope of the present disclosure as long as they contain all the features of the corresponding independent claims. The ventilator arrangement 1 is connected to a subject 2, which here is illustrated in the form of a pair of lungs. The subject might, for example, be a human or an animal. The connection might be to the respiratory tract of the subject, for example via mouth, nose, trachea, or the like.

The ventilator arrangement 1 can comprises pressure regulating means 3 arranged to apply a pressure to the airways of the patient 2. The ventilator arrangement 1 can further comprise at least one pressure and/or flow sensor 4a-4c for obtaining pressure and/or flow measurements. Furthermore, the ventilator arrangement 1 can comprise a control unit 5 for monitoring a pressure and/or flow based on the pressure and/or flow measurements obtained by the pressure and/or flow sensors 4a-4c, and/or for controlling the pressure regulating means 3 based on the monitored pressure and/or flow.

In one example, the pressure regulating means 3 comprises a controllable inspiratory valve 3a for regulating the pressure applied to the airways of the subject 2 during inspiration. In one example, the pressure regulating means 3 comprises a controllable expiratory valve 3b for regulating the pressure of the airways of the subject 2 during expiration. It should be appreciated that the pressure regulating means 3 could be realised in many different ways. For example, the inspiratory valve 3a may be exchanged for a blower or any other means capable of controlling the pressure to the airways of a patient.

During inspiration, the control unit 5 can control the inspiratory valve 3a to regulate the pressure applied to the airways of the subject 2 by regulating a flow of breathing gas supplied to the patient via an inspiratory line 6. The ventilator arrangement 1 can further comprise gas mixing means 7. The gas mixing means 7 can be coupled to one or more internal or external gas sources 8a-8c for the supply of pressurised breathing gas.

During expiration, the control unit 5 can control the expiratory valve 3b to regulate the pressure of the airways of the subject 2 by regulating a flow of exhalation gases exhaled by the subject 2 via an expiratory line 9. The exhalation gases are then vented out, for example to ambient air or a scavenging system through a vent 10 of the ventilator arrangement 1. The setup of pressure and/or flow sensors 4a-4c may vary in dependence of the intended function of the ventilator arrangement 1. In one embodiment, the ventilator arrangement 1 comprises a pressure sensor 4a arranged in or close to a Y-piece 11, for example to measure a proximal pressure substantially corresponding to the airway pressure of the subject 2. The Y-piece 11 can connect the inspiratory line 6 and expiratory line 9 with a subject connector 12, such as a patient interface. The inspiratory line 6, the expiratory line 9, and the subject connector can be part of a patient circuit. A patient circuit can be part of a breathing circuit. In one embodiment, the ventilator arrangement 1 comprises a first flow sensor 4b arranged in the inspiratory line 6 to measure the flow of gas inhaled by the subject 2. In one embodiment, the ventilator arrangement 1 comprises a second flow sensor 4c arranged in the expiratory line 9 to measure the flow of gas exhaled by the subject 2. It should be emphasised that the pressure sensor 4a alternatively or additionally can be a flow sensor. Any of the first and/or second flow sensors 4b-c can alternatively or additionally be a pressure sensor. Although not shown in the drawing it should be appreciated that the sensors 4a-4c can be connected to the control unit 5, for example in order for the control unit to control the pressure regulating means 3, for example based on pressure and/or flow values directly obtainable through the sensors 4a-4c, and/or derivable by the control unit 5 from the measured values.

The control unit 5 might be configured to detect when the subject 2 wants to go from one respiratory phase to the other, i.e. from inspiration to expiration or vice versa, and to switch respiratory phase accordingly.

The ventilator arrangement 1 is arranged to apply a set positive end-expiratory pressure, PEEP, level for performing the ventilation.

The ventilator arrangement 1 may comprise input means 16. The input means 16 can be any kind of input means, such as, for example, a button, a keyboard, a switch, a touchscreen, a connection to an external input means, a mouse, a microphone, or the like. The input means 16 can comprise several of the aforementioned input means, such as several switches, and/or a combination of one or several of the aforementioned input means, such as switches and a touchscreen. The input means 16 can be arranged to receive user input. The input means can be arranged to transfer the user input to the control unit 5. The control unit can for example be an electronic circuit. The control unit can for example be a control computer.

The control unit 5 can comprise a computer program stored on a memory 13 in the control unit 5. The computer program can cause the control unit 5 to perform partly or fully a method according to the present disclosure. Examples of such methods are described in relation to FIGS. 2a and 2b. As an example, a method according to the present disclosure can be performed when executed by a processor 14 of the control unit 5. The computer program may also be installed on an external computer which may be connected to the control unit 5 of the ventilator arrangement 1 to make it perform the steps of the method.

The ventilator arrangement 1 may comprise output means 17. The output means 17 can be any kind of output means, such as, for example, a screen, a display, a lamp, a speaker, a printer, a connection to an external output means, a tactile output means, such as a vibrating output means, or the like. The output means 17 can comprise several of the aforementioned output means, such as several lamps, and/or a combination of one or several of the aforementioned input means, such as a screen and a speaker. The output means 17 can be arranged to give output information to a user. The output means can be arranged to receive the output from the control unit 5.

The ventilator arrangement 1 can be a ventilator arrangement for maintaining the end expiratory lung volume, EELV, of a subject when an external manoeuvre is performed on the subject ventilated by the ventilator arrangement.

Figure 2B:
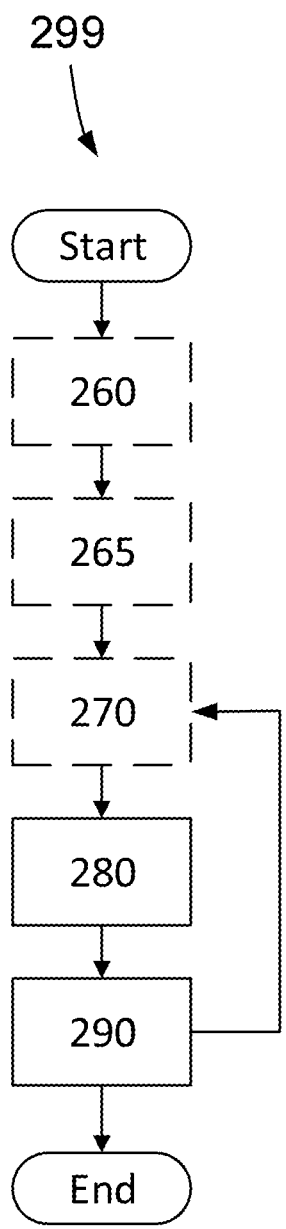
FIG. 2b shows, in a schematic way, a method according to a second example of the present invention.

The ventilator arrangement can be arranged to perform any of the methods described in relation to FIGS. 2a and 2b.

The ventilator arrangement 1 can be arranged to determine start conditions. The start conditions can include at least breathing circuit leakage. As an example, the breathing circuit leakage can be determined, for example by the control unit, based on measurement values of the first and/or second flow sensor 4b, 4c. This is described in more detail in relation to FIG. 2a-b. The start conditions can comprise determining a tidal volume, TV, of the subject 2.

The ventilator arrangement 1 can be arranged to performing a ventilation pause in the ventilation of the subject. This is preferably performed prior to the external manoeuvre. In one example, this is achieved by controlling the regulating means 3. In one example, this achieved by closing the inspiratory valve 3a and/or the expiratory valve 3b. The control unit 5 can thus be arranged to close the inspiratory valve 3a and/or the expiratory valve 3b for performing a ventilation pause. The control unit 5 can be arranged to control the inspiratory valve 3a and the expiratory valve 3b so that the flow through them is balanced for achieving a pause in ventilation.

The ventilator arrangement 1 can be arranged to initiate the pause of the ventilation based on a user action on the input means 17. As an example, the ventilation pause might be initiated based on a received press on a button and/or based on a received voice command. Any other user action on any other input means might be used as well for initiating the pause of the ventilation.

The ventilator arrangement 1 can be arranged to pause the ventilation of the subject during an expiration phase. The ventilator arrangement 1 can be arranged to pause the ventilation of the subject during an inspiration phase. More details regarding the pausing of ventilation are described in relation to FIG. 2a.

The ventilator arrangement 1 can be arranged to determine a possible change in airway pressure, ΔPaw, of the subject during pausing of the ventilation. This is further described in relation to FIG. 2a. As an example, the possible change in airway pressure can be determined by the control unit 5 based on at least two measurement values from the pressure sensor 4a.

The ventilator arrangement 1 can be arranged to resume the ventilation of the subject after the external manoeuvre. When resuming, an updated set level for the PEEP is applied. The updated set level basically corresponds to the sum of the set PEEP level prior to pausing the ventilation and the determined possible change in airway pressure, ΔPaw, of the subject. When resuming the ventilation, the ventilator arrangement can be arranged to do the resumption at a first pre-determined time period after pausing the ventilation, and/or based on a user input, for example a user input on the input means 17. More details regarding the assumption are given in relation to FIG. 2a. As an example, the updated set level for the PEEP might be applied by the control unit 5.

The ventilator arrangement 1 can be arranged to indicate the resumption of the ventilation a second pre-determined time period prior to resuming the ventilation. This indication might be performed by the output means 17, for example via a visible signal, a tactile signal and/or an audio signal.

The ventilator arrangement 1 and/or suitable components thereof can be arranged to perform the method 200 and/or any of the steps described in relation to the method 200. The ventilator arrangement 1 and/or suitable components thereof can be arranged to perform the method 299 and/or any of the steps described in relation to the method 299.

Figure 3A:
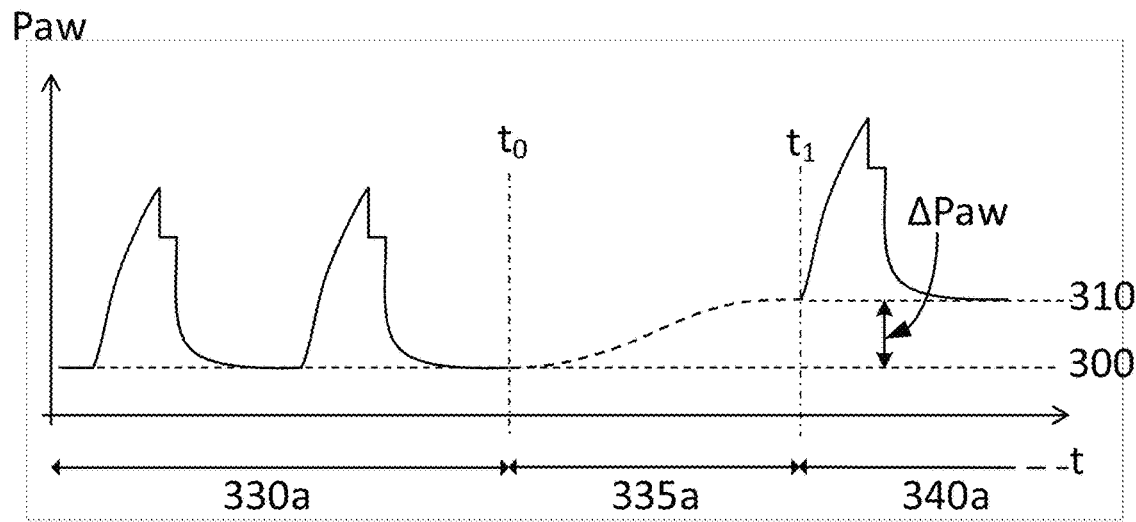
FIG. 3a shows, in a schematic way, an example of a first situation in which a method according to the first example of the present disclosure can be used.
Figure 3B:
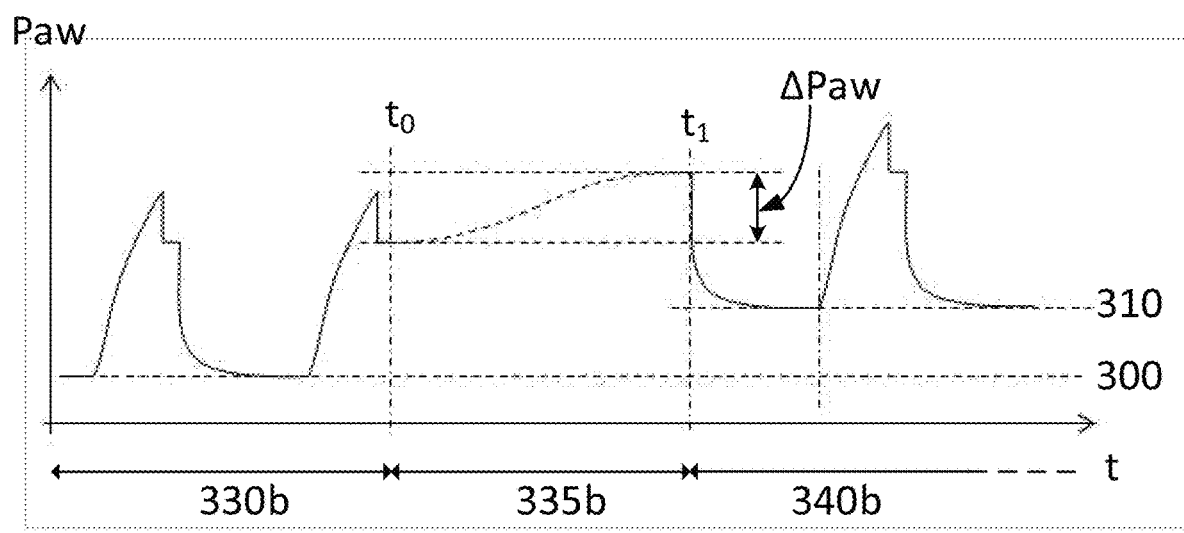
FIG. 3b shows, in a schematic way, an example of a second situation in which a method according to the first example of the present disclosure can be used.

FIG. 2a shows, in a schematic way, a method 200 according to a first example of the present invention. The method 200 is a method for controlling a ventilator arrangement for maintaining the end expiratory lung volume, EELV, of a subject when an external manoeuvre is performed on the subject ventilated by the ventilator arrangement. Herein, the ventilator arrangement applies a set positive end-expiratory pressure, PEEP, level for performing the ventilation. The method 200 can be applied to control the ventilator arrangement 1 described in relation to FIG. 1, or any other suitable ventilator arrangement. The method 200 can, for example, partly or fully be performed by a computer program, for example a computer program at the control unit 5. Examples of a first and a second situation in which the method 200 can be used are shown in FIG. 3a and FIG. 3b, respectively. The method 200 is especially suitable for handling of external manoeuvres with comparably fast changes of the external pressure, such as changing position of a subject, for example putting a subject into a Trendelenburg position or back. However, the method might be stopped or paused, as will be explained later, in case this is deemed necessary during the manoeuvre, for example for adapting tubes or cables which are connected to the subject and which might need to be rearranged during a manoeuvre. The method 200 starts with the optional step 210.

The optional step 210 comprises determining start conditions including at least breathing circuit leakage. It is known in the art how breathing circuit leakage of a ventilator arrangement can be determined. The practical steps to perform the determination might depend on the design of the breathing circuit. As an example, the breathing circuit leakage can be determined based on measurements from the first flow sensor 4b and the second flow sensor 4c, such as a difference between the measured flow from the first flow sensor 4b and the second flow sensor 4c over one breathing cycle. In one example the leakage is determined via a so-called insp-hold-manoeuvre, for which the inspiration is paused for a pre-determined time period, for example for 10 seconds, and for which a change in pressure is determined, for example via pressure sensor 4a. In case it is determined that the pressure has been dropped more than a pre-determined threshold it might be determined that a leakage is present.

The first and the second situation depicted in FIG. 3a and FIG. 3b depict the airway pressure, Paw, of a subject evolving over time t. The time is denoted on the horizontal axis as indicated by the letter t. In the shown situations, the airway pressure starts from a first base level 300, rises first during inspiration and then settles shortly on a basically constant level, which is higher than the base level 300, but generally lower than the highest value during inspiration. This basically constant level is often denoted inspiratory hold. The inspiratory hold can be considered to be part of the inspiration phase. The airway pressure then decreases again from the basically constant level to the base level 300 during expiration. Thus, a first time period 330a in the first situation consists basically of two full breathing cycles and finishes at the end of an expiration phase. A first time period 330b in the second situation consists roughly speaking of one and a half breathing cycles and stops at the end of an inspiration phase. During the first time periods 330a, 330b, the ventilator arrangement operates usually in normal operation mode regarding ventilation of the subject.

The determining of the starting conditions can comprise reading stored values, for example from the memory 13. As an example, the ventilator arrangement might be arranged to determine the values for the start conditions at other occasions and store these values so that they are present once the method 200 is performed. Thus, the term "determining" can refer to a read-out procedure where a previously determined value is stored. The previously determined value does not necessarily need to be stored in the ventilator arrangement. As an example, an operator could note any previously determined values and, for example, enter any previously determined value to the ventilator arrangement at a later moment of time if needed, for example via the input means 16.

The optional step 210 can be performed automatically. The optional step 210 can be performed manually.

The optional step 210 is preferably performed prior the external manoeuvre starts. However, this is not a necessary condition. As an example, in case step 210 comprises a read-out of a stored value, this can be performed even at a later time. Step 210 is preferably performed when the ventilator arrangement is operated in normal operation mode. In the shown situations, step 210 might thus be preferably performed during the first time periods 330a, 330b, or any time earlier. The method continues with the optional step 215.

The optional step 215 comprises receiving user input. The user input might be received via input means of the ventilator arrangement, such as pressing a button or the like. User input might be received via any of the input means 16 described in relation to FIG. 1, or via any other means. The optional step 215 can also be performed prior step 210. As an example, step 210 might be started based on received user input. Step 210 might be started directly or some time period after user input is received. Step 215 can comprise receiving at least one time period as input, such as a value for any of the time periods described in relation to method 200. The method continues with step 220.

Step 220 comprises performing a ventilation pause in the ongoing ventilation of the subject. The ventilation pause is performed prior to the external manoeuvre. In the first and second situation the ventilation pause is performed at a first moment of time to. The ventilation pause might be initiated by a manual action on an input means of the ventilator arrangement. The ventilation pause might be initiated by receiving user input in step 215. The ventilation pause might start directly after user input is received. The ventilation pause might start a pre-determined time period after user input has been received.

The ventilation of the subject can be paused during an expiration phase. The ventilation might be paused at a specific point of an expiration phase, such as the end of the expiration phase. This situation is depicted in FIG. 3a and thus part of the first situation.

The ventilation of the subject can be paused during an inspiration phase. The ventilation might be paused at a specific point of an inspiration phase, such as the end of the inspiration phase. This situation is depicted in FIG. 3b and thus part of the second situation. The end of the inspiration or expiration phase might thus be specific points chosen for initiating a pause in ventilation However, in principle, in case a specific point of a breathing cycle is chosen, any specific point might be chosen, i.e., for example, even any point in between start and end of an inspiration/expiration phase.

The pre-determined time-period after which a ventilation pause might start might comprise a specific amount of time, such as a specific number of seconds, for example five seconds. The pre-determined time-period after which a ventilation pause might start might comprise a time-period until a certain event occurs, such as a time period until a specific point in the breathing cycle is reached. The pre-determined time period is in one example long enough so that the optional step 210 can be performed during the pre-determined time period. In one example, the optional step 210 is performed during the pre-determined time-period.

By initiating the pausing by receiving user input, flexibility is achieved. As an example, the user input might be given when all preparations for the external manoeuvre are finished. The pausing of the ventilation might be indicated to a user of the ventilation arrangement, for example via output means.

The external manoeuvre is intended to be performed after the ventilation is paused, i.e. after to. In the shown situations, the external manoeuvre is preferably performed during the second time period 335a, 335b. The second time period 335a, 335b might in practice be considerably longer than the period shown in the figures. As an example, the second time period might comprise several ordinary breathing cycles. It should be emphasised that the external manoeuvre generally is not performed during the whole second time period 335a, 335b as it might be impossible to directly start the external manoeuvre. However, the external manoeuvre is preferably started directly or shortly after to. The method continues with step 230.

Step 230 comprises determining a possible change in airway pressure, $\Delta Paw$, of the subject during pausing of the ventilation. The airway pressure might, for example, be determined via the pressure sensor 4a described in relation to FIG. 1. A possible change in airway pressure can thus be determined via the difference of at least two different measurements, thus as at least two different measurements of the pressure sensor 4a. In one example, a first airway pressure is determined when the pausing starts, i.e. at $t_0$ when referring to FIG. 3a or 3b, and a second airway pressure is determined when the ventilation is resumed, i.e. at $t_1$ when referring to FIG. 3a or 3b. It is in principal enough to determine the possible change in airway pressure based on these two values. However, intermediate values for $\Delta Paw$ can also be determined continuously and/or intermittently during the pause of the ventilation. The final $\Delta Paw$ can then be determined as the sum of the intermediate values for $\Delta Paw$. $\Delta Paw$ can be positive, negative, or basically zero. As an example, during an external manoeuvre which comprises pressurising the abdomen with $CO_2$, or which comprises putting a subject in a Trendelenburg position it is expected that $\Delta Paw$ will be positive. On the other hand, when putting a subject back into the horizontal position after the Trendelenburg position, it is expected that $\Delta Paw$ will be negative. Even a so-called inverse Trendelenburg position might be used, for which the signs of $\Delta Paw$ will be interchanged compared to the above situation. It should be emphasised, that the final value for $\Delta Paw$ determined in step 230 corresponds to the difference in airway pressure between pausing the ventilation and resuming the ventilation. The method continues with the optional step 240.

The optional step 240 comprises indicating the resumption of the ventilation a second pre-determined time period prior to resuming the ventilation. This indication might be performed via any of the output means 17 described in relation to FIG. 1, or via any other means. As an example, the indication might be via a sound and/or via a lamp, for example a blinking lamp. This can give a warning that the external manoeuvre should be finished, or at least paused, prior the resumption of the ventilation. The pre-determined time period is preferably chosen in such a way that enough time will be left to finish, abort, or pause the manoeuvre. As an example, the pre-determined time period might be around 1, 2, 3, 4, or 5 seconds. The method continues with the optional step 245.

The optional step 245 comprises receiving user input. Anything described in relation to receiving user input in step 215 applies to step 245 as well. As an example, a user of the ventilation arrangement might give user input when the external manoeuvre is finished. The method continues with step 250.

Step 250 comprises resuming the ventilation of the subject after the external manoeuvre. In the shown situations, the ventilation is resumed at a second moment of time $t_1$. The resumption might be initiated based on the received user input from step 245. As an example, the ventilation is resumed directly after the user input is received, or a pre-determined time-period afterwards. This allows resuming the ventilation as soon as the external manoeuvre is finished, so that no unnecessarily long pause of ventilation is applied to the subject.

In one example, the resumption of the ventilation starts at a first pre-determined time period after pausing the ventilation. The pre-determined time period might be chosen in such a way that the subject will tolerate well the pausing of the ventilation. In the shown situations, the pre-determined time period might correspond to the second time period 335a, 335b. The first pre-determined time period might be determined by a user of the ventilator arrangement. The first pre-determined time period can, for example, be entered to the ventilator arrangement via input means, such as the input means 16. In one example, the first pre-determined time period might be chosen in an interval of 2-30 seconds.

In one example, the ventilation is resumed based on the first pre-determined time period and the possible receiving of a user input, whichever might cause the earliest resumption. Thus, unnecessary pauses can be avoided, even if the time for performing the external manoeuvre might not be exactly foreseen.

When resuming, the ventilation is preferably resumed at the same state of the breathing cycle as when the ventilation was paused. As an example, in case the ventilation is paused at the end of the expiration phase, the resumption of the ventilation will continue at the end of the expiration phase. This is usually the most natural choice as it usually will be most safe for the subject. In the depicted first and second situation, i.e. FIGS. 3a and 3b, the ventilation is resumed in the same phase of the breathing cycle as when the ventilation was paused.

When performing step 250, i.e. when resuming the ventilation of the subject after the external manoeuvre, an updated set level for the PEEP is applied. The updated set level for the PEEP, $setPEEP_{new}$, basically corresponds to the sum of the set PEEP level prior to pausing the ventilation, $setPEEP_{old}$, and the determined possible change in airway pressure, $\Delta Paw$, of the subject. In other words, $setPEEP_{new} \approx setPEEP_{old} + \Delta Paw$. In one example, the sign $\approx$ is replaced by equality.

In the first and second situation depicted in FIGS. 3a and 3b, the set PEEP level prior to pausing the ventilation can correspond to the base level 300. The updated set level for the PEEP can correspond to an updated base level 310. That $setPEEP_{new}$ and $setPEEP_{old}$ relate to each other as in the above equation is immediately evident in the first situation as the ventilation is paused on the base level 300, i.e. at $setPEEP_{old}$, and resumed directly at the updated set PEEP level, i.e. the updated base level 310. However, the above relation applies equally well at the second situation, as the difference between the base level 300 and the updated base level corresponds basically to $\Delta Paw$.

The ventilation is then preferably continued in normal operation mode after the resumption, i.e. after $t_1$. This is illustrated by the third time period 340a, 340b, where the ventilation is continued in normal operation mode, although with an updated set PEEP level.

In one example, the method 200 ends after step 250. This might be especially suitable in case the external manoeuvre has been finished or aborted.

In one example, the pausing is initiated by pressing a button, for example during step 215. The ventilation might then be paused as long as the button is pressed. In one example, the resumption of the ventilation is initiated by releasing the button, for example during step 245. This combination assures that a user is close to the ventilator arrangement 1 during the pausing at any time. Thus, it is assured that the ventilation pause can be aborted, i.e. the ventilation be resumed, at any time at very short notice. This can further increase the safety of the subject as the ventilation might be resumed immediately in case any complications are discovered.

In one example, the external manoeuvre is divided in several sub-steps with pauses in between the sub-steps. The method 200 can then be repeated for each sub-step of the external manoeuvre. As an example, it might be determined that the external manoeuvre will take so much time, that the ventilation might not be continuously paused during that time without endangering the health of the subject. The external manoeuvre might then be divided into sub-steps in such a way that the ventilation might be safely paused for the time period of each sub-step. The method 200 can then repeatedly be performed for each sub-step of the external manoeuvre.

When repeating the method 200, one or several steps can be omitted in the repetition. As an example, step 210 might be sufficient to perform once at the start of the method and it might thus not be needed to perform that step at every repeated run of the method 200. Even other steps might be skipped during repetition, such as any of the steps relating to receiving user input.

The method 200 has been described above in a specific order. However, the method can also be performed in any other order and/or at least partly in parallel as long as one step does not necessarily require the finishing of a previous step.

It should also be emphasised that a ventilator arrangement according to the present disclosure, or a suitable element thereof, can be arranged to perform any of the steps described in relation to method 200.

FIG. 2b shows, in a schematic way, a method 299 according to a second example of the present invention. The method 299 is a method for controlling a ventilator arrangement for achieving a desired end expiratory lung volume, EELV, when an external manoeuvre is performed on a subject ventilated by the ventilator arrangement. The ventilator arrangement applies a set positive end-expiratory pressure, PEEP, level for performing the ventilation. The desired EELV can be that the EELV is kept basically constant. The desired EELV can be a lower or a higher EELV than the current EELV. The desired EELV can be that the EELV is increased or decreased with a pre-determined amount. The desired EELV can be a desired change in the EELV.

The method 299 is especially suitable for handling of external manoeuvres with comparably slower changes of the external pressure, such as pressurising the abdomen with $CO_2$. The method 299 starts with the optional step 260.

The optional step 260 comprises determining whether a leakage is present in the breathing circuit. This is performed prior performing the external manoeuvre. A warning is outputted in case the presence of a leakage has been determined. The warning might be dependent on that the leakage is above a pre-determined threshold. The determination of the leakage can be as described in relation to step 210 of method 200. The warning can be outputted via the output means 217, for example as an audio signal, a visual warning, or a tactile signal. The warning will give a user the possibility to abort the method or to try to reduce and/or to eliminate the leakage. The method continues with the optional step 265.

The optional step 265 comprises determining an offset between inspired and expired lung volume, VTi–VTe, prior the external manoeuvre. This is in one example performed by the first and/or the second flow sensor 4b, 4c. This is in one example performed by a flow sensor at the position of the pressure sensor 4a. An example of determining the offset is given in FIG. 6a-b, where different quantities are plotted over one breathing cycle. FIG. 6a depicts a measured flow ¢, for example at the position of the sensor 4a, over time t. As can be seen, the flow is first positive during a first time period 600. This corresponds to the inspiration phase of a breathing cycle. The flow is then basically constant during a second time period 610. This corresponds to the inspiratory hold period. The flow is then negative during a third time period 620. This corresponds to the expiration phase. The integration of the flow during the first time period 600, i.e. the first hatched area 630 over the first time period 600, corresponds to the inspired tidal lung volume VTi of a breathing cycle of the subject. The integration of the flow during the third time period 620, i.e. the second hatched area 640 over the third time period 620, corresponds to the expired tidal lung volume VTe of a breathing cycle of the subject.

The summed up ventilation volume V at every given time t is depicted in FIG. 6b, wherein the situation of FIG. 6b corresponds to the same situation as which is depicted in FIG. 6a. At the start the summed up ventilation volume V is zero and raises then during the first time period 600 until inspired tidal lung volume VTi is reached, which is indicated by the first arrow 650. The height of the V-curve at the first arrow 650 corresponds to the first hatched area 630. The summed up tidal lung volume V then falls during the third time period 620, in total with the expired tidal lung volume VTe, which is indicated by the second arrow 660. The difference in height of the V-curve as indicated by the second arrow 660 corresponds to the second hatched area 640. As can be seen in the shown example, the inspired and the expired tidal lung volumes are not equal. This might, for example, be caused due to leakage, due to measurement errors, due to chemical or biological processes, or due to any other reasons. As an example, an offset might be caused by gas exchange in the lungs of the subject. The offset between inspired and expired lung volume will in the following be denoted as $(VTi-VTe)_{offset}$. The method continues with the optional step 270.

If step 265 is performed, the external manoeuvre is preferably started after this step. Step 270 is also optional and if performed the external manoeuvre is preferably started in the beginning of or during step 270. The method will work equally well in case the external manoeuvre is started during or after the first or after several repetitions of the steps 270-290. The repetition of steps 270-290 will be described later. If method 299 only comprises steps 280 and 290, the manoeuver is preferably started in the beginning of or during step 280. The method will work equally well in case the external manoeuvre is started during or after the first or after several repetitions of the steps 280-290.

In the optional step 270 a flow of breathing gas to and/or from the subject is determined. This might, for example, be performed via the first and/or the second flow sensor 4b, 4c. The method continues with step 280.

Step 280 comprises determining a difference between inspired and expired tidal lung volume of a breathing cycle of the subject. This can be performed in the same way as described in relation to step 265. The difference between inspired and expired tidal lung volume will in the following be denoted with (VTi–VTe) or (VTi–VTe), when the difference refers to a specific run n of the method. It should be emphasised that the offset in step 265 relates to the fact that the external manoeuvre has not yet been started, whereas the difference in step 280 might be determined irrespective of whether the external manoeuvre has already been started or not. The inspired and/or expired lung volume can be determined based on the determined flow of breathing gas during step 270. The inspired and/or expired lung volume can also be determined in any other way. The method continues with step 290.

Step 290 comprises adjusting the PEEP level after the breathing cycle of the subject based on the determined difference so that the desired EELV of the subject is achieved. The adjustment of the PEEP level might also be based on the determined offset. If step 265 is not performed, the offset between inspired and expired lung volume, $(VTi-VTe)_{offset}$, may be assumed to be zero. In this case the determined difference between inspired and expired tidal lung volume of the breathing cycle can be assumed to reflect a change in end expiratory lung volume of the subject during the breathing cycle, caused by the external manoeuvre. The desired EELV can be a difference in EELV, setΔEELV, in relation to the current EELV. Step 290 can in one example be achieved via the following set of equations:

$$PEEP_{new} = PEEP_{old} + \Delta PEEP,$$

$$\Delta PEEP = K_1 \cdot \Delta VT + K_2 \cdot set\Delta EELV,$$

$$\Delta VT = VTi - VTe - (VTi - VTe)_{offset}.$$

Herein, $K_1$ and $K_2$ denote control parameters. These control parameters might be defined as $K_1=\kappa_1 \cdot Ers$ and $K_2=\kappa_2 \cdot Ers$, wherein $\kappa_1$ and $\kappa_2$ are dimensionless constants, for example in the order of magnitude of 1. In one example, $K_1$ and $K_2$ are chosen to be in the range 0.2-2, for example 0.2 and 0.5. They might be chosen to operate a used control circuit in a stable way and might be adjusted according to the used hardware. Ers denotes the respiratory elastance and can in one example be determined as Ers=ΔP/VT over one breathing cycle, wherein ΔP denotes $PAW_{ei}-PAW_{ee}$, i.e. the difference between in the PAW between the end of an inspiration phase and the end of an expiration phase, and VT denotes the tidal volume. In one example, Ers is determined together with $(VTi-VTe)_{offset}$, for example during step 265. It should be emphasised that the above definitions of the control parameters and of Ers only are examples. Many different variations can apply and the specific definitions and the specific determination of these quantities will depend on the specific design of the ventilator arrangement.

ΔVT represents the above mentioned change in end expiratory lung volume of the ventilated subject, which change is hence determined based on a difference (VTi–VTe) between inspired and expired tidal lung volume of a current breathing cycle and a determined or assumed difference $((VTi-VTe)_{offset})$ between inspired and expired tidal lung volume of a breathing cycle prior to the external manoeuvre, herein referred to as the offset between inspired and expired lung volume. As clear from above, the offset is a non-manoeuvre induced difference between inspired and expired tidal lung volume of the ventilated subject, which offset may be measured prior to the manoeuvre (step 265) or be assumed to be zero.

When the change in end expiratory lung volume, ΔVT, has been determined from the difference between inspired and expired tidal lung volume and the determined or assumed offset, a PEEP adjustment value, ΔPEEP, is determined based on the determined change in end expiratory lung volume and (if any) the desired difference in EELV of the subject, setΔEELV. Once the PEEP adjustment value has been determined, PEEP may be adjusted to a new level, $PEEP_{new}$, based on the previous PEEP level, $PEEP_{old}$, and the determined PEEP adjustment value.

The steps 280 and 290 and, optionally, the step 270, are repeated for several breathing cycles, at least during the external manoeuvre, and preferably for basically each breathing cycle during the external manoeuvre. It might be possible to "jump over" some repetitions of these steps during the external manoeuvre, but in many cases the performance of these steps during each or basically each breathing cycle will give the best results.

When repeating the above named steps, the above set of equations can be adapted to $$PEEP_{n+1} = PEEP_n + \Delta PEEP,$$

$$\Delta PEEP_n = K_1 \cdot \Delta VT - K_2 \cdot (\Sigma \Delta VT_k - set\Delta EELV),$$

$$\Delta VT_n = VTi_n - VTe_n - (VTi - VTe)_{offset},$$

wherein n+1 denotes the new PEEP level and n the old PEEP-level. The summation Σ runs over k=1 up to k=n, and n denotes the number of repetitions so far.

In one example, the repeated steps are repeated for less than about 50 or for less than about 100 breathing cycles. This can assure that unknown small measurement errors will not add up to large deviations of the PEEP level compared to the desired behaviour. In one example, the repeated steps are repeated for less than 10 steps, less than 20 steps, less than 30 steps, less than 40 steps, less than 50 steps, less than 60 steps, less than 70 steps, less than 90 steps, or less than 100 steps. In one example, the repeated steps are repeated for less than 120 steps, less than 150 steps, less than 170 steps, or less than 200 steps.

After the desired number of repetitions the method 299 ends. In one example the desired number of repetitions, i.e. the number of breathing cycles for which the method is performed, might be adjusted or determined by a user, for example via input means.

The method 299 thus adapts the PEEP level after each breathing cycle without the need to pause the ventilation. The PEEP level is preferably adapted in such a way that the lung volume of the subject is kept constant. Thus, this method might be applied even in case a pause in ventilation might not be safely applied to the subject.

Figure 4A:
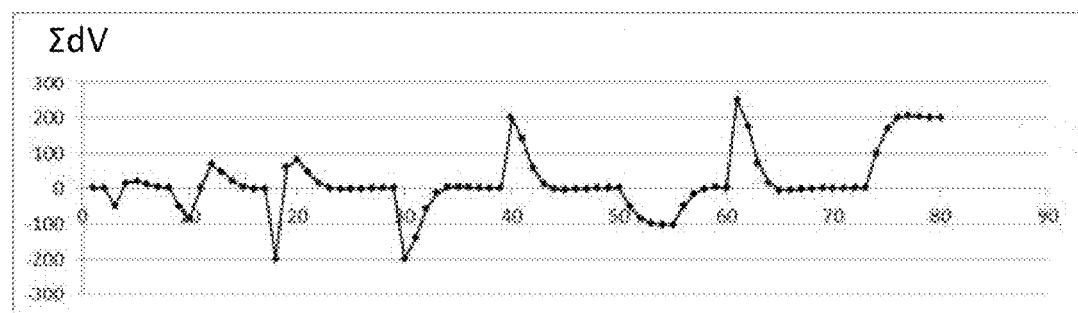
FIG. 4a-d show, in a schematic way, an example of a third situation in which a method according to the second example of the present disclosure can be used.
Figure 4B:
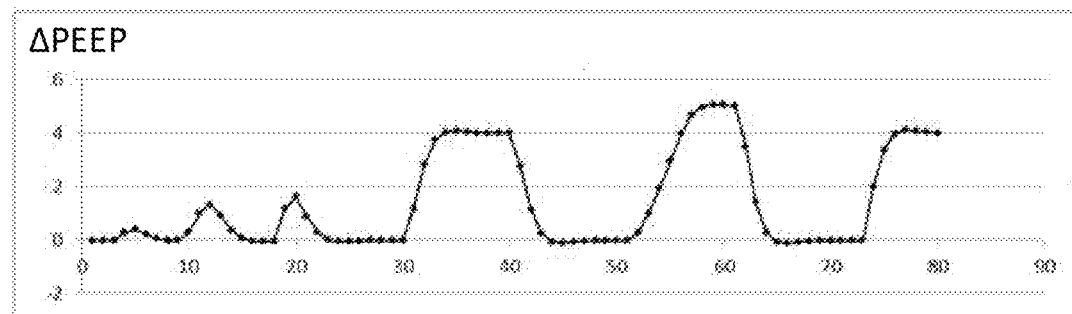
Figure 4C:
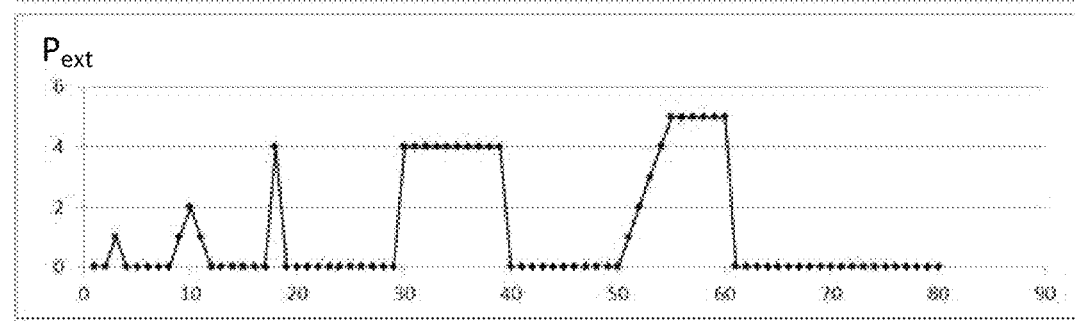
Figure 4D:
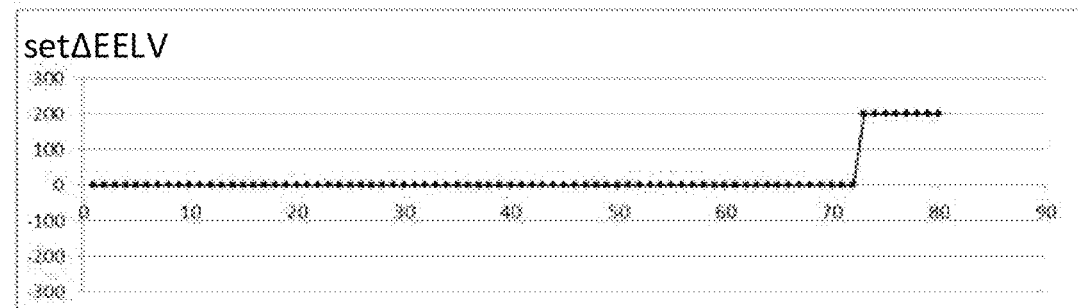

Examples of situations in which the method 299 can be applied are given in FIG. 4*a-d* and FIG. 5*a-c*. In all these figures the horizontal axis denotes the number of breathing cycles. In FIG. 4*a* and FIG. 5*a* the vertical axis denotes a total change in lung volume of the subject in arbitrary units, wherein the change is denoted in respect to the first breathing cycle. In FIGS. 4*b* and 5*b* the vertical axis denotes an adjustment of the PEEP level in arbitrary units. The adjustment of the PEEP level is in relation to the PEEP level of the first breathing cycle. In FIGS. 4*c* and 5*c* the vertical axis denotes an additional pressure on the lungs of the subject in arbitrary units. The additional pressure is in relation to the pressure of the first breathing cycle and might originate from the external manoeuvre. In FIG. 4*d* the vertical axis denotes a desired change in setEELV. Consequently, FIG. 5*a-c* depict a situation in which no change in the EELV is desired. FIG. 4*a-d* depict all the same third situation. FIG. 5*a-c* depict all the same fourth situation.

The application of the method 299 will first be described in relation to the fourth situation, depicted in FIG. 5*a-c*. When referring to FIG. 5*c*, the external manoeuvre causes a comparably small rise 510 of the pressure over 20 breathing cycles. Afterwards, the additional pressure is constant 520 over some breathing cycles and declines 530 then somewhat faster to the level prior the external manoeuvre over 10 breathing cycles. Finally, at the end, an external manoeuvre rises the pressure rapidly 550 over only one breathing cycle. It should be emphasised that the present disclosure is and has been described in relation to an external manoeuvre, but is equally well applicably in relation to any other cause of external pressure on the lungs of the subject.

The control algorithm, for example the set of equations as described in relation to step 290, will adjust the PEEP level in response to the pressure exhibited to the lungs so as to maintain the EELV. As can be seen from FIG. 5*a* and FIG. 5*b*, the lung volume deviates 515 during the first, slow, rising period of the pressure only slowly from the EELV at the first breathing cycle and the PEEP level basically follows the shape of the curve in FIG. 5*c* with a slight delay. After the external pressure remains constant after the rising period, the PEEP level is with some delay kept constant as well and the difference in EELV completely compensated for 525 so that the EELV is on the same level as in the first breathing cycle.

The falling of the external pressure is, as described above, somewhat faster than the rising. The PEEP delay in FIG. 5*b* appears again and the difference in EELV is now slightly bigger 535 due to the faster change in the pressure. After the pressure is constant again, the PEEP level gets constant as well and the difference in EELV does eventually appear again 545. The second, short, rise of external pressure causes again a delay in adjusting the PEEP level and, due to the faster rising of the pressure, for some breathing cycles a larger difference 555 in EELV before the control algorithm has adapted the PEEP level and the difference in EELV has disappeared again 565. As can be seen, the PEEP level is not adapted instantaneously and the EELV is not instantaneously kept constant. This is due to the control algorithm. The time of adaptation and/or the difference can depend on the speed of changing the external pressure. However, eventually the adaptation of the PEEP level is performed and the difference in EELV will disappear after a relatively short number of breathing cycles.

FIG. 4*a-d* depict a third situation in which the method 299 is used. The graphs in these figures behave in the same way as described in relation to the fourth situation. In addition, it is depicted in the figures how the control algorithm might affect the PEEP level and the difference in EELV in case the rising and falling of the external pressure does not only appear at different "speed", but also up to different heights and/or without first remaining on a stable level before falling again.

Shortly after the seventieth breathing cycle, a new set level for the EELV is desired, as indicated in FIG. 4*d*. This is without any change in the external pressure as can be seen in FIG. 4c. Due to the new set level for EELV, the control algorithm rises the PEEP level although no change in the external pressure appears. Due to rising of the PEEP level and due to the absence of a change in external pressure to the lungs, a deviation in the EELV appears, as can be seen in FIG. 4a, and eventually remains, as desired by the new set level for the EELV in FIG. 4d.

The method 299 can perform any of the features described in relation to FIG. 4a-d and FIG. 5a-c.

It should also be emphasised that a ventilator arrangement according to the present disclosure, or a suitable element thereof, can be arranged to perform any of the steps described in relation to method 299.

Furthermore, it should be emphasised that the first method 200 (FIG. 2a) for maintaining the end expiratory lung volume of the ventilated subject by adjusting PEEP based on a change in airway pressure determined during a ventilation paus may be advantageously combined with the second method 299 (FIG. 2b) for achieving a desired end expiratory lung volume of the ventilated subject by adjusting PEEP based on a difference between inspired and expired tidal lung volume of a breathing cycle of the subject.

For example, it may be advantageous to apply the first method for trying to maintain the end expiratory lung volume of the subject during the external manoeuvre, and to apply the second method during a final phase of the external manoeuvre and/or after the external manoeuvre, after having resumed ventilation of the subject with the updated set level for PEEP determined in accordance with the first method. In this way, any change in end expiratory lung volume caused by the external manoeuvre and not fully compensated for by the first method, or any retroactive effect on the end expiratory lung volume of the subject caused by the external manoeuvre but occurring after having performed the first method, can be detected and compensated for by the second method. Thereby, the second method may serve to ensure that the EELV of the subject is maintained at a substantially constant level after resuming ventilation of the subject with the updated set level for PEEP. The second method may also be performed after the first method in order to change, in a controlled manner, the EELV of the subject to a new desired EELV of the subject following the external manoeuvre.

Consequently, according to an aspect of the present disclosure, there is provided a method for controlling a ventilator arrangement for achieving a desired EELV of the subject when an external manoeuvre is performed on a subject ventilated by the ventilator arrangement, wherein the ventilator arrangement applies a set PEEP level for performing the ventilation, the method comprising the steps of:
a) performing a ventilation pause in the ongoing ventilation of the subject prior to the external manoeuvre;
b) determining a possible change in airway pressure, ΔPaw, of the subject during pausing of the ventilation;
c) resuming ventilation of the subject after at least parts of the external manoeuvre, wherein an updated set level for the PEEP is applied, wherein the updated set level basically corresponds to the sum of the set PEEP level prior to pausing the ventilation and the determined ΔPaw;
d) determining a difference between inspired and expired tidal lung volume of a breathing cycle of the subject, and
e) adjusting the set PEEP level after the breathing cycle of the subject based on the determined difference so that the desired EELV of the subject is achieved, wherein steps d) and e) may be repeated for several breathing cycles during and/or after the external manoeuvre.

As discussed above, the desired EELV may be a new desired EELV or an EELV corresponding to the EELV of the subject prior to the external manoeuvre.

Steps d) and e) are performed, and typically repeatedly performed, after resuming ventilation of the subject in step c). In some situations and/or for some types of external manoeuvres, steps a)-c) may be performed during the external manoeuvre whereas steps d) and e) are performed, and typically repeatedly performed, after the external manoeuvre. In other situations and/or for other types of external manoeuvres, steps a)-c) may be performed during a first phase of the external manoeuvre whereas steps d) and e) are performed, and typically repeatedly performed, during a second and final phase of the external manoeuvre and/or after the external manoeuvre.

Steps a)-c) correspond to method steps of the first method 200 described above with reference to FIG. 2a, whereas steps d)-e) correspond to method steps of the second method 299 described above with reference to FIG. 2b. It should thus be realised that steps a)-c) may be performed in accordance with any of the teachings described above with reference to FIG. 2a, whereas steps d)-e) may be performed in accordance with any of the teachings described above with reference to FIG. 2b.

For example, the method may comprise the steps of determining a change in end expiratory lung volume of the subject based on the determined difference between inspired and expired tidal lung volume, and adjusting the PEEP level after the breathing cycle of the subject based on the determined change in end expiratory lung volume.

It may also comprise the steps of determining or assuming an offset between inspired and expired lung volume of the subject prior to the external manoeuvre, and determining the change in end-expiratory lung volume of the subject based on the determined difference between inspired and expired tidal lung volume and the determined or assumed offset.

As discussed above, the step of adjusting the PEEP level may comprise the steps of determining a PEEP adjustment value, ΔPEEP, based on the determined change in end expiratory lung volume of the subject and the desired constant EELV of the subject, and adjusting the PEEP level to a new PEEP level based on a previous PEEP level and the PEEP adjustment value.

According to a another aspect of the disclosure, there is provided a computer program product, comprising instructions which, when the program is executed by a computer, cause the computer to carry out the above-described method steps a)-e).

According to yet another aspect of the disclosure, there is provided a computer-readable medium comprising instructions which, when executed by a computer, cause the computer to carry out the above described method steps a)-e).

The computer may be a computer of the control unit 5 of the ventilator arrangement 1 (see FIG. 1) or an external computer which may be connected to the control unit 5.

The method may thus be performed by the ventilator arrangement 1 described above with reference to FIG. 1. Consequently, according to another aspect of the present disclosure, there is provided a ventilator arrangement 1 for achieving a desired EELV of a subject when an external manoeuvre is performed on the subject ventilated by the ventilator arrangement, the ventilator arrangement being arranged to apply a set PEEP level for performing the ventilation, the ventilator arrangement further being arranged to:
  a) perform a ventilation pause in the ongoing ventilation of the subject prior to the external manoeuvre;
  b) determine a possible change in airway pressure, ΔPaw, of the subject during pausing of the ventilation;
  c) resume ventilation of the subject after at least parts of the external manoeuvre, wherein an updated set level for the PEEP is applied, wherein the updated set level basically corresponds to the sum of the set PEEP level prior to pausing the ventilation and the determined ΔPaw;
  d) determine a difference between inspired and expired tidal lung volume of a breathing cycle of the subject, and
  e) adjust the set PEEP level after the breathing cycle of the subject based on the determined difference so that the desired EELV of the subject is achieved,
  wherein the ventilator arrangement may be arranged to perform steps d) and e) repeatedly for several breathing cycles during and/or after the external manoeuvre.

Consequently, it should be realized that the method 200 for maintaining the end expiratory lung volume of the ventilated subject by adjusting PEEP based on a change in airway pressure determined during a ventilation paus, described above with reference to FIG. 2a, and the method 299 for achieving a desired end expiratory lung volume of the ventilated subject by adjusting PEEP based on a difference between inspired and expired tidal lung volume of a breathing cycle of the subject, described above with reference to FIG. 2b, may be performed separately or in sequence, and that the ventilator arrangement and computer program product for carrying out the method(s) may be adapted accordingly.

The invention claimed is:

1. A method for controlling a ventilator arrangement for maintaining an end expiratory lung volume ("EELV"), of a subject when an external manoeuvre is performed on the subject ventilated by the ventilator arrangement, wherein the ventilator arrangement applies a set positive end-expiratory pressure ("PEEP") level for performing a ventilation, the method comprising:
  performing a ventilation pause in the ongoing ventilation of the subject prior to the external manoeuvre;
  determining a possible change in airway pressure (ΔPaw) of the subject during pausing of the ventilation; and
  resuming the ventilation of the subject after at least parts of the external manoeuvre, wherein an updated set level for the PEEP is applied, wherein the updated set level basically corresponds to the sum of the set PEEP level prior to pausing the ventilation and the determined possible change in airway pressure (ΔPaw) of the subject,
  wherein the external manoeuvre comprises pressurizing an abdomen of the subject with $CO_2$ so that a lung volume of the subject is affected.

2. The method according to claim 1, wherein the pausing of the ventilation is initiated by a received user input at an input means of the ventilator arrangement.

3. The method according to claim 1, wherein the resumption of the ventilation starts at a first pre-determined time period after pausing the ventilation.

4. The method according to claim 3, further comprising the step of indicating the resumption of the ventilation a second pre-determined time period prior to resuming the ventilation.

5. The method according to claim 1, wherein the ventilation of the subject is paused during an expiration phase or during an inspiration phase.

6. The method according to claim 1, wherein the external manoeuvre is divided in several sub-steps with pauses in between the sub-steps, and wherein the method is repeated for each sub-step of the external manoeuvre.

7. The method according to claim 1, further comprising the step of determining start conditions including at least breathing circuit leakage.

8. A ventilator arrangement for maintaining an end expiratory lung volume ("EELV") of a subject when an external manoeuvre is performed on the subject ventilated by the ventilator arrangement, the ventilator arrangement being arranged to apply a set positive end-expiratory pressure ("PEEP") level for performing a ventilation, the ventilator arrangement further being arranged to:
  performing a ventilation pause in the ventilation of the subject prior to the external manoeuvre;
  determining a possible change in airway pressure (ΔPaw) of the subject during pausing of the ventilation; and
  resuming the ventilation of the subject after at least parts of the external manoeuvre, wherein an updated set level for the PEEP is applied, wherein the updated set level basically corresponds to the sum of the set PEEP level prior to pausing the ventilation and the determined possible change in airway pressure (ΔPaw) of the subject,
  wherein the external manoeuvre comprises pressurizing an abdomen of the subject with $CO_2$ so that a lung volume of the subject is affected.

9. The ventilator arrangement according to claim 8, wherein the ventilator arrangement is arranged to initiate the pause of the ventilation based on a user action on an input means of the ventilator arrangement.

10. The ventilator arrangement according to claim 8, wherein the ventilator arrangement is arranged to resume the ventilation at a first pre-determined time period after pausing the ventilation.

11. The ventilator arrangement according to claim 10, wherein the ventilator arrangement is further arranged to indicate the resumption of the ventilation a second pre-determined time period prior to resuming the ventilation.

12. The ventilator arrangement according to claim 8, wherein the ventilator arrangement is further arranged to pause the ventilation of the subject during an expiration phase or during an inspiration phase.

13. The ventilator arrangement according to claim 8, wherein the ventilator arrangement further is arranged to determine start conditions including at least breathing circuit leakage.

14. A non-transitory computer-readable data storage medium comprising instructions which, when executed by a computer, cause the computer to carry out the method according to claim 1.

* * * * *